United States Patent [19]
Olschefski

[11] Patent Number: 4,730,484
[45] Date of Patent: Mar. 15, 1988

[54] MISSING BEARING DETECTOR

[76] Inventor: Robert Olschefski, 3410 Center Rd., Highland, Mich. 48013

[21] Appl. No.: 876,778

[22] Filed: Jun. 20, 1986

[51] Int. Cl.⁴ .................. G01M 15/00; G01H 1/08
[52] U.S. Cl. .................. 73/119 R; 73/593; 73/660
[58] Field of Search .................. 73/118.1, 119 R, 570, 73/572, 593, 609, 649, 658, 660, 661

[56] References Cited

U.S. PATENT DOCUMENTS

| | | | |
|---|---|---|---|
| 2,502,601 | 4/1950 | Stanfield | 73/119 R |
| 3,023,609 | 3/1962 | Schubring | 73/593 |
| 3,400,578 | 9/1968 | Frarey et al. | 73/119 R |
| 3,697,865 | 10/1972 | Smith et al. | 73/118 |
| 4,377,947 | 3/1983 | Matsushita et al. | 73/593 |
| 4,424,709 | 1/1984 | Meier, Jr. et al. | 73/117.3 |
| 4,448,063 | 5/1984 | Mudge et al. | 73/115 |
| 4,493,042 | 1/1985 | Shima et al. | 73/593 |
| 4,545,249 | 10/1985 | Matay | 73/609 |
| 4,550,604 | 11/1985 | Sugimoto et al. | 73/593 |

FOREIGN PATENT DOCUMENTS

| | | | |
|---|---|---|---|
| 842861 | 7/1952 | Fed. Rep. of Germany | 73/118.1 |
| 0090133 | 6/1982 | Japan | 73/593 |
| 0317945 | 10/1971 | U.S.S.R. | 73/118.1 |
| 427262 | 12/1974 | U.S.S.R. | 73/119 R |
| 453602 | 12/1974 | U.S.S.R. | 73/117.3 |

OTHER PUBLICATIONS

American Heritage Dictionary, p. 149, 1976.

*Primary Examiner*—Stewart J. Levy
*Assistant Examiner*—Robert R. Raevis
*Attorney, Agent, or Firm*—Krass & Young

[57] ABSTRACT

A missing bearing detector for an internal combustion engine in which the engine, at an early stage in the assembly process, is tested on the assembly line by rotating the crankshaft to move the piston assemblies through their reciprocal cycles; microphones are placed near the engine to pick up high intensity noises indicative of missing bearing parts; and encoder signals are generated for transmission to a comparator where they are compared to the noise signals generated by the microphones to indicate whether a bearing is missing and to indicate the particular piston assembly in which the bearing is missing. The detector also functions to distinguish between upper and lower bearing shell halves by noting whether relatively low level or relatively high level thresholds are violated by the fault signal and also distinguishes between pairs of piston assembiles moving in phased relationship by providing a pair of microphones axially spaced along the engine to thereby generate relatively high intensity and relatively low intensity fault signals depending upon the distance of the respective microphone from the faulty piston assembly.

15 Claims, 6 Drawing Figures

MISSING BEARING DETECTOR

BACKGROUND OF THE INVENTION

This invention relates to methods and apparatus for detecting missing, misaligned or mislocated parts in machine assemblies. More specifically, this invention relates to a method and apparatus for detecting missing bearings in an engine assembly.

The assembly of a multicylinder internal combustion engine is a very complicated process requiring precise coordination between a plurality of humans and a plurality of machines, each employed at various stages in the process of forming the engine assembly. Whereas much progress has been made in the area of quality control with respect to engine assembly, it is still not uncommon for an engine to be assembled with one or more parts missing or misplaced. Specifically, as an engine is assembled, a bearing insert or shell is manually inserted into the bearing housing at the crankshaft end of the connecting rod. The connecting rod is then positioned against the respective pin on the crankshaft, the other bearing insert or shell half is manually inserted into the bearing cap, and the bearing cap with insert is positioned over the exposed half of the crankshaft pin and buttoned down to the connecting rod to complete the bearing assembly between the connecting rod and the crankshaft. On occassion, an operator either fails to insert one or both of the inserts or the insert is inserted but becomes misplaced before final assembly of the bearing is accomplished. In either case, the completed engine is missing one or both of the bearing inserts and will soon destroy itself in actual operation.

Various methods and apparatus have been proposed to detect missing bearings in the completed engine assembly. In the most commonly used technique, the engine is substantially totally assembled, at least to the point where the lubricating passages within the engine are complete; oil is supplied to the engine, the engine is spun; and the oil pressure is monitored to detect a drop in pressure corresponding to a missing bearing insert in a particular piston subassembly. Whereas this system is generally effective, it occurs at such a late stage in the assembly process that correction of the detected problem requires essentially complete disassembly of an essentially completed engine. It has also been proposed to pump air through the oil passages and monitor the air pressure to detect a missing bearing insert but this procedure can also be performed only at such time as the engine has been completed to the point of establishing the oil passages and therefore also entails essentially complete disassembly of an essentially completed engine in situations where a missing bearing insert is detected. Both of these prior art techniques also are rather time consuming and involve rather complex support apparatus, in the one case to supply pressurized oil to the engine assembly and in the other case to provide pressurized air to the engine assembly.

SUMMARY OF THE INVENTION

This invention is directed to the provision of a method and apparatus for readily and efficiently detecting the presence of missing, misaligned, or mislocated parts in a machine assembly.

More specifically, this invention is directed to the provision of a method and apparatus for detecting missing bearing inserts in an engine assembly at an early stage in the process of assembling the engine so as to allow the ready repair of the engine.

In its broadest form, the invention provides a method of detecting missing, misaligned or misplaced parts in a machine assembly of the type in which a plurality of subassemblies are driven through reciprocal cycles in response to rotation of a central shaft. The invention method comprises the steps of rotating the central shaft to move the subassemblies through their respective cycles; generating a plurality of code signals for each rotation of the shaft in timed relation to the shaft rotation; sensing the level of acoustical vibration in the vicinity of the machine assembly during rotation of the shaft; generating a fault signal in response to a sensed acoustical vibration in excess of a predetermined magnitude; and comparing the code signals with the fault signals to determine the presence of a missing, misaligned or misplaced part. This arrangement provides an inexpensive and effective method of locating a missing or misaligned part and allows the detection to occur at a relatively early stage in the assembly process.

The disclosed embodiment of the invention is particularly suited for detecting missing or mislocated parts in a multicylinder engine assembly of the type including a crank shaft and a plurality of piston assemblies associated with the respective cylinders. In the disclosed embodiment, the methodology comprises rotating the crankshaft of the engine assembly; generating a plurality of code signals for each rotation of the crankshaft in timed relation to the crankshaft rotation; sensing the level of acoustical vibration in the vicinity of the engine assembly during rotation of the crankshaft; generating a fault signal in response to a sensed acoustical vibration in excess of a predetermined magnitude; and comparing the code signals and the fault signals to determine whether a bearing insert is missing from the engine assembly and the particular piston assembly from which the part is missing. This method allows the early and efficient detection of a missing bearing insert in multicylinder engine assemblies moving along an assembly line.

According to a further feature of the invention, the signal generating means comprises an angle encoder operative to generate a plurality of equally spaced pulse signals for each revolution of the crankshaft and a marker signal each time the crankshaft passes through a given angular position. This arrangement keys the fault signals to a specific point in the angular rotation of the crankshaft and thereby enables the precise determination of the particular piston assembly in which the bearing part is missing.

According to a further feature of the invention, the crankshaft is rotated by a motor and the motor also drives the angle encoder. This arrangement provides a compact package and simplifies the synchronization as between the crankshaft and the encoder.

According to a further feature of the invention, the crankshaft of the engine assembly includes key means, the motor engages the end of the crankshaft and locates angularly on the crankshaft key means, and the marker signal is generated at a fixed angular position related to the angular position of the crankshaft key means. This arrangement further facilitates the precise identification of the particular piston assembly in which the bearing is missing.

According to a further feature of the invention, a plurality of indicator means are provided respectively corresponding to the cylinders of the engine assembly and a comparator is provided for receiving the code signals and the fault signals. The comparator operates to selectively activate or fail to activate each of the indicator means depending on the presence or absence or a fault signal at the point of rotation of the crankshaft corresponding to a transitional position in the reciprocal cycle of the piston assembly operating in the corresponding cylinder of the engine assembly.

In the disclosed embodiment of the invention, the apparatus includes a carrier mounted for movement relative to the assembly line between a rest position clear of the assembly line and a working position adjacent the engine assembly to be tested, and the motor, encoder, and acoustical pick-up device are mounted on the carrier. This arrangement allows the various components of the invention detection system to be readily moved into and out of association with the engine to be tested.

As specifically disclosed, the invention is related to engine assemblies of the V8 type, the pick-up device includes a pair of microphones, and the carrier includes a portion positioning the microphones in spaced relation over the engine assembly with the driver of the motor engaging the crankshaft of the engine assembly. This arrangement provides the ability to distinguish between two piston assemblies of a V8 engine moving in phase with each other.

DETAILED DESCRIPTION OF THE PREFERRED EMBODIMENT

Figure 1:
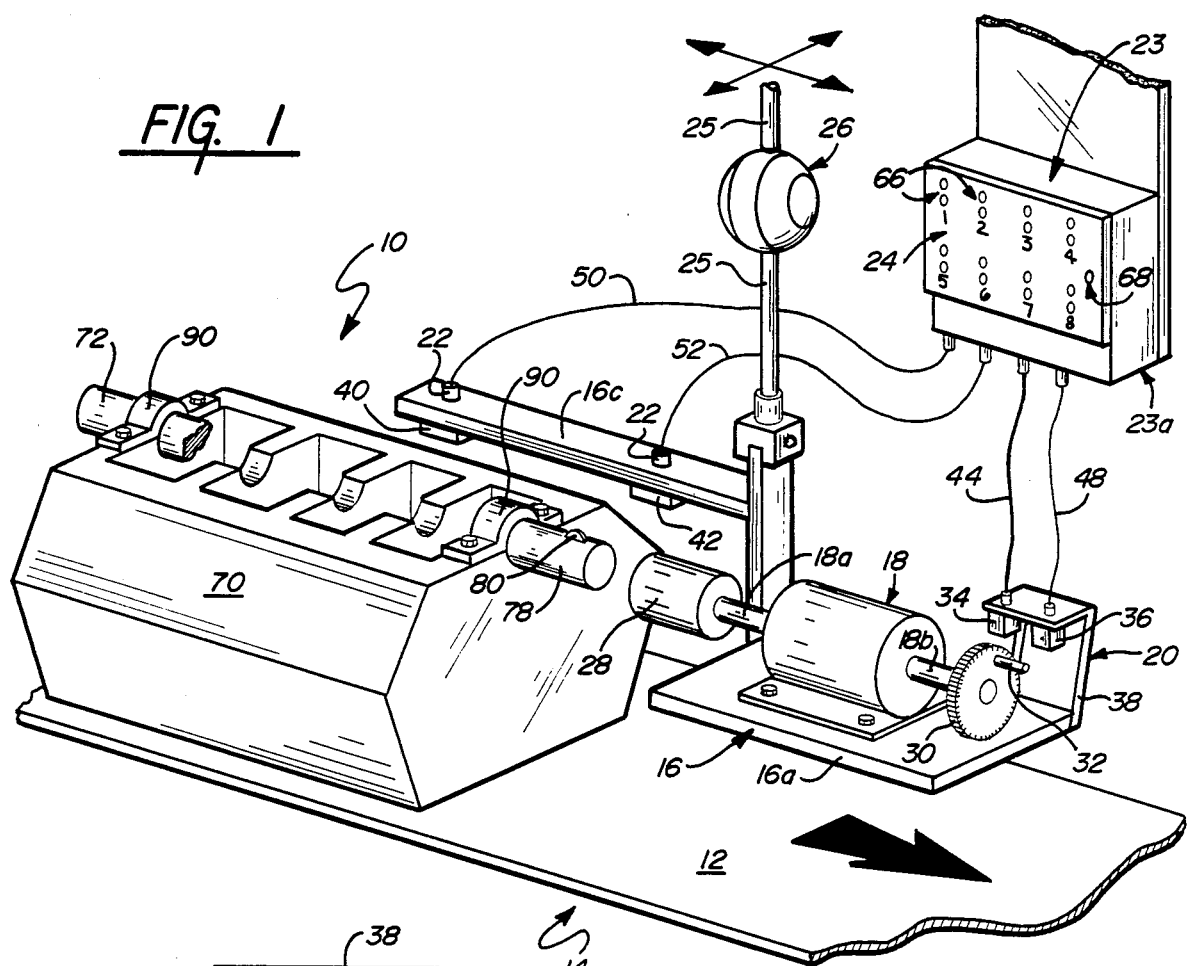
FIG. 1 is a perspective, somewhat schematic view of a missing bearing detector according to the invention.
Figure 3:
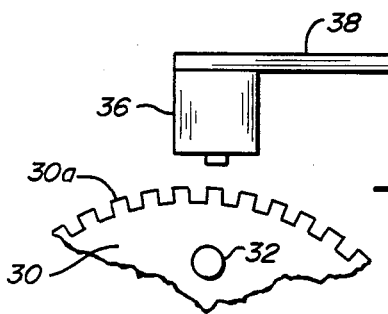
FIGS. 2 and 3 are fragmentary detail views of portions of the missing bearing detector of FIG. 1.
Figure 2:
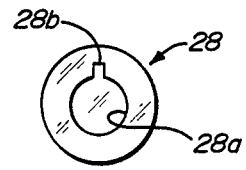
Figure 4:
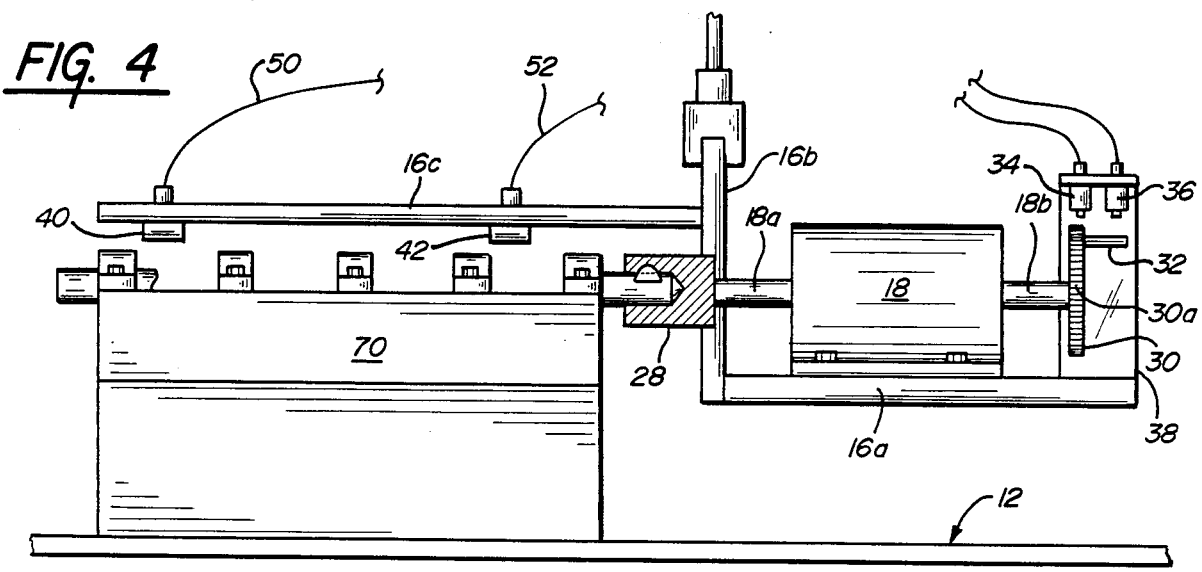
FIG. 4 is a schematic side elevational view of the invention missing bearing detector.

The invention missing bearing detector is shown in FIG. 1 in association with an assembly line for internal combustion engines. In the assembly line, as schematically depicted, engine assemblies 10 are moved successfully along a conveyor belt 12 past a work station 14 at which the missing bearing detector is located.

The missing bearing detector includes a carrier 16, a motor 18, an encoder device 20, a pick-up device 22, a comparator 23, and an indicator panel 24.

Carrier 16 is shown schematically and includes a base portion 16a, a bracket portion 16b, and a cantilever portion 16c. Carrier 16 is suspended from a overhead track by a cable 25 engaging the upper end of carrier bracket portion 16b and coacting with a spring balancer 26. Balancer 26 coacts with an overhead trolley (not shown) engaging a network of overhead rails to allow the carrier to be moved both parallel and transversely with respect to the conveyor 12 as well as up and down.

Motor 18 is mounted on base portion 16a of carrier 16 and includes a rearward drive shaft 18a secured to a driver 28. Driver 28 includes a central bore 28a and a keyway 28b. Motor 18 may comprises many of several forms including an air motor, a hydraulic motor, or an electric motor.

Encoder 20 includes an encoder wheel 30, a lug 32, and a pair of proximity switches 34 and 36.

Encoder wheel 30 is secured to the free end of forward motor drive shaft 18b and includes 360 teeth 30a corresponding to the 360 degrees of a single revolution. Lug 32 is suitably secured to encoder wheel 30 at a point adjacent the outer perimeter of the wheel. Proximity switches 34 and 36 are positioned respectively over wheel 30 and lug 32 by an angle bracket 38 secured to base portion 16a of carrier 16. Proximity switches 34, 36 may take any of various forms and may for example comprise a hall effect proximity switch. Whatever their specific form, proximity switch 34 detects the passage of each individual tooth 30a of wheel 30 and proximity switch 36 detects the once per revolution passage of lug 32.

Pickup device 22 comprises a pair of microphones 40 and 42 positioned in spaced relation on cantilever portion 16c of carrier 16. When used with a V8 engine of the type illustrated, cantilever portion 16c of carrier 16 functions to position microphones 40 and 42 in axially spaced relation over the engine with microphone 42 positioned generally adjacent the front 10a of the engine and microphone 40 positioned generally adjacent the rear 10b of the engine. Microphones 40,42 may comprise any known type of accoustical microphone.

Figure 6:
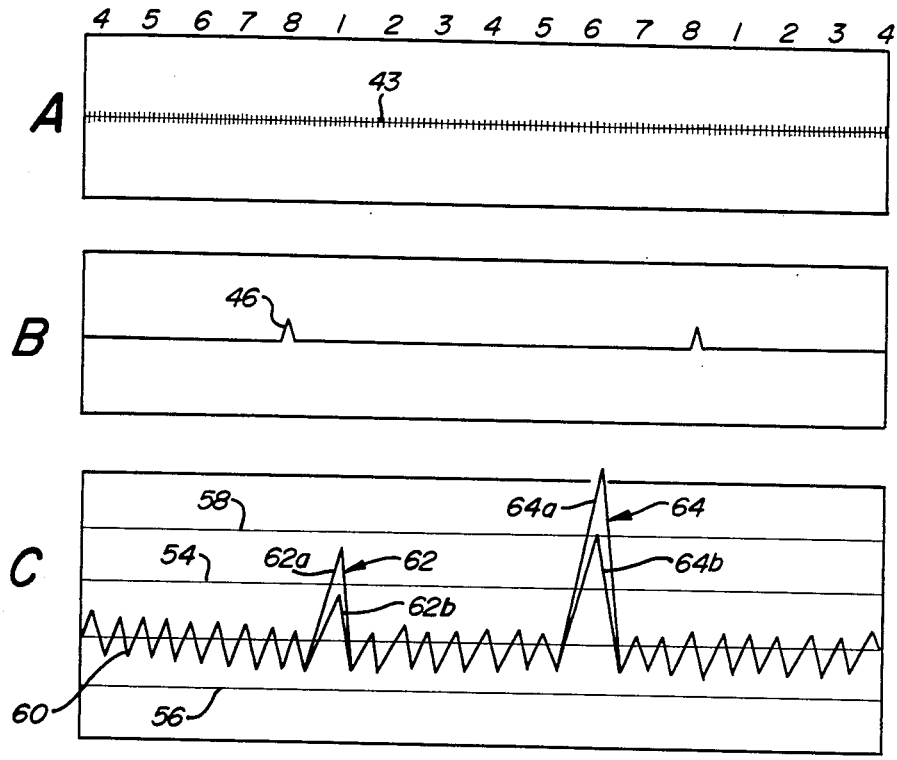
FIG. 6 is a view showing the methodology of a comparator system used in the invention missing bearing detector.

Comparator 23 includes a housing 23a housing suitable electronic comparator equipment capable of generating the three channels A, B and C seen in FIG. 6. Channel A is generated by proximity switch 34 of encoder 20 and includes 360 equally spaced pulse signals for each revolution of the crank shaft transmitted to the comparator via line 44. Channel B is generated by proximity switch 36 of encoder 20 and comprises a marker signal 46 corresponding to each revolution of the crankshaft transmitted to the comparator by line 48. Channel C is generated by the output of microphones 40, 42 as transmitted to the comparator through lines 50 and 52. Channel C includes thresholds 54 and 56 corresponding to normally encountered background noise in the typical engine assembly environment and a further, higher threshold 58. The signal 60 generated on channel C normally moves between thresholds 54 and 56 but, as illustrated, may generate fault signals 62 violating threshold 54 or fault signals 64 violating thresholds 54 and 58.

Indicator panel 24 includes a plurality of indicator lights 66, corresponding to the cylinders of the engine assembly 10, and an engine approval light 68.

In the illustrated embodiment, the engine assemblies are of the V8 type and include a block 70, a crankshaft 72, and a plurality of piston assemblies respectively associated with the crankshaft and with the cylinders of block 70. Crankshaft 72, in known manner, includes a plurality of throws 74, a plurality of pins 76 extending selectively between the throws, and a front end portion 76 including the usual key 80 for drivingly engaging a timing gear. Each piston assembly includes a connecting rod 82 secured at one end in known manner to the wrist pin of the piston of the piston assembly and secured in known manner at its other end to a crankshaft pin 76 of the crankshaft. The connection of the connecting rod to the crankshaft is constituted by a lower bearing member defined by the upper end 82a of the connecting rod; an upper bearing member defined by bearing cap 84; a semicircular lower hearing shell or insert 86 seated in bearing member 82a; and an upper semicircular bearing shell or insert 88 seated in bearing cap 84. The connecting rod 82 and cap 84 are typically formed of cast iron or aluminum and the inserts or shells 86 and 88 are typically formed of a Babbitt metal, that is, a soft silvery antifriction alloy composed of tin with small amounts of copper and antimony.

The engine assemblies 10 arriving at test station 14 are positioned pan face up so that the crankshaft is presented at the upper face of the assembly.

In operation, the engine assemblies 10 arriving on conveyor belt 12 at test station 14 are individually tested to detect missing bearing shells. The testing may be done while the engines are moving continuously through the test station or the engines may be momentarily stopped at the test station to facilitate the testing operation.

In either case, as the engine assemblies arrive at the test station, carrier 16 is moved from a rest position clear of the assembly line to a working position in which driver 42 is engaged with the end 78 of the crankshaft with driver slot 28b keying on key 80 to locate the driver positively with respect to the crankshaft and locate key means 80 positively with respect to lug 32. For example, key 28b may be angularly aligned with lug 32. With driver 28 engaging crankshaft end 78, cantilever portion 16c of carrier 16 extends rearwardly over the block of the engine to dispose microphone 42 adjacent the front end of the engine and dispose microphone 40 adjacent the rear end of the engine.

Motor 18 is now energized to drive shaft 18a and thereby driver 28 to rotate crankshaft 72 of the engine assembly and move the piston assemblies through their reciprocal cycles. As motor 18 drives the crankshaft, encoder wheel 30 coacts with proximity switch 34 to generate a plurality of equally spaced pulse signals 43 on channel A of encoder 23; lug 38 coacts with proximity switch 36 to generate marker pulses 46 on channel B of the comparator at fixed angular positions related to the angular position of key means 80; and microphones 40,42 generate a signal 60 on channel C of the comparator. If signal 60 remains within thresholds 54 and 56 throughout the duration of the test, comparator 23 functions to supply a signal to approval light 68 to illuminate the light and thereby indicate to the operator that the engine is satisfactory. If, however, signal 60 violates a threshold during the course of the test, the comparator functions to signal one of the indicator lights 66 to indicate an absence of a bearing shell in the piston assembly corresponding to that light.

Figure 5:
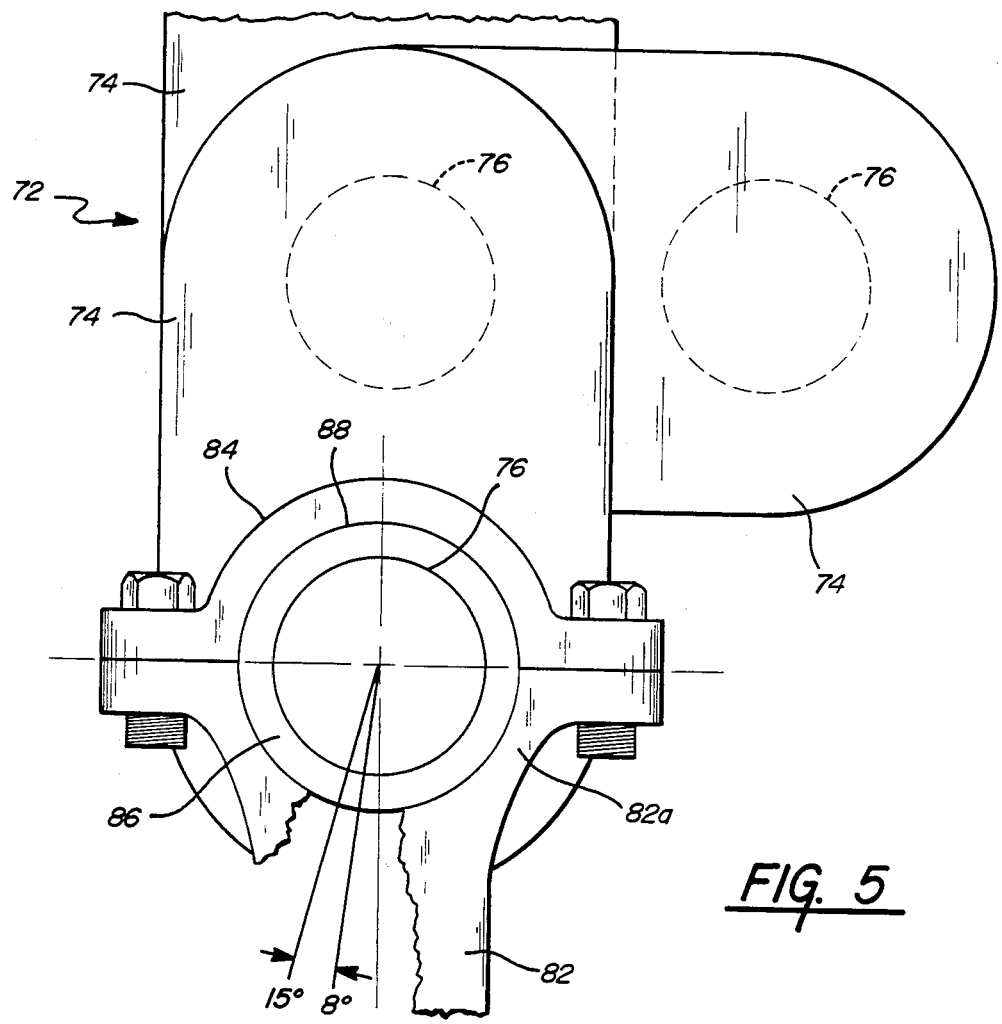
FIG. 5 is a view of a crankshaft, showing in detail the bearing construction at the connection between the connecting rod of a piston assembly and the corresponding crankshaft pin of the crankshaft.

Specifically, as a connecting rod 82 of a particular piston assembly approaches the bottom dead center position as seen in FIG. 5, the linear downward movement of the piston assembly ceases and the piston assembly moves instantaneously through a lull period in which there is substantially no linear movement. At about 8 degrees in the cycle past bottom dead center, the piston assembly begins its upward linear movement. It is at this transitory point in the reciprocating cycle of the piston assembly that the absence of a shell 86 or 88 is detected by a noise which is sensed by microphones 40,42. Based on the geometry of the parts, the critical phase of the reciprocating cycle of the piston assembly occurs between 8 degrees and 15 degrees past bottom dead center during which period, in the event that one of the inserts 86,88 is missing, the crankshaft pin 76 moves relative to bearing 82a or bearing cap 84 to take up the slack in the bearing assembly created by the absence of shell 86 or 88. The relative movement between the pin 76 and the associated connecting rod bearing surfaces causes a significant, readily detectable slapping noise which is picked up by the microphones and transmitted to the comparator to generate a fault signal 62,64 violating the thresholds of the channel and thereby indicating the absence of a bearing shell.

The presence of any fault signal violating threshold 54,56 indicates a missing shell or detector, and the particular piston assembly in which the shell is missing can be readily determined by virtue of pulse signals 43 and marker signals 46 which, when compared to the position at which the fault signal occurred, and given the knowledge that the fault signal will occur between 8 degrees and 15 degrees past bottom dead center of the particular piston assembly, enables the comparator to readily identify the piston assembly involved.

One microphone would be sufficient to identify the involved piston assembly in engines wherein each assembly is at all times out of phase with respect to each other piston assembly, such for example as a V6 engine. However, in a V8 engine or a straight 4 cylinder engine, all of the piston assemblies are not out of phase with respect to each other but in fact pairs of piston assemblies at any given time are in phase so that it is necessary to distinguish between the pairs of piston assemblies. This is done in the disclosed embodiment by the use of the spaced microphones positioned forwardly and rearwardly with respect to the engine assembly. Since the pairs of piston assemblies that are in phase are spaced forwardly and rearwardly along the piston axis, the front and rear microphones will pick up different levels of noise intensity depending upon the forward or rearward location of the involved piston assembly so that the fault signal will include a higher spike 62a, 64a generated by the microphone nearest the involved piston assembly and a lesser spike 62b, 64b generated by the microphone remote from the involved piston assembly. The comparator may thus function to readily distinguish between pairs of piston assemblies that are in phase with respect to each other so that in all cases the specific piston assembly in which the bearing insert is missing can be positively identified.

The invention missing bearing detector is also able to distinguish between the upper and lower insert or shell halves. Specifically, if the lower shell half 86 is missing, the crankshaft pin 76 will slap against the upper shell half 88. Since the Babbitt material of the shell halves is relatively soft, a relatively low intensity fault signal 62 will be generated which will violate only threshold line 54. If, however, the upper insert half is missing, the crankshaft pin 76 will slap against the adjacent hard metal of the bearing cap 84 and generate a high intensity fault signal 64 which will violate both threshold line 54 and threshold line 58. The invention bearing detector thus functions to not only identify the specific piston assembly in which a bearing shell is missing but also to identify whether the upper or lower bearing shell half is missing. If the upper shell is missing, the comparator functions to illuminate the upper light of the pair of lights 66 provided for each cylinder, and if the lower shell is missing, the lower light of that pair is illuminated.

The comparator is also desirably programmed to not transmit a fault signal to an indicator light 66 unless and until the fault signal occurs with respect to any particular piston assembly during a predetermined percentage of successive revolutions of the crankshaft. For example, the comparator may be programmed to initiate a fault signal only if the signal occurs in 9 out of 10 successive crankshaft revolutions. This assures that an extraneous environmental noise will not result in the indication of a missing insert.

The invention bearing detector will be seen to provide an inexpensive and efficient means of detecting the presence or absence of a missing bearing shell. Since the missing part is detected early in the assembly process, the engine can be readily withdrawn from the assembly line and readily torn down to replace the missing part as compared to prior art devices in which the engine was essentially completed before the absence of the missing part was detected. The invention bearing detector also minimizes capital investment and maintenance requirements since the pressurized oil systems, or the pressurized air systems, of the prior art detection devices are no longer required but rather are replaced by the inexpensive, readily available, low maintenance microphones which "listen" to the engine and inexpensively and efficiently deliver a fault signal indicating the presence and the location of a missing bearing.

Whereas a preferred embodiment of the invention has been illustrated and described in detail, it will be apparent that various changes may be made in the disclosed embodiment without departing from the scope or spirit of the invention.

I claim:

1. A method of detecting missing parts in a multicylinder engine assembly of the type including a crankshaft and a plurality of out of phase piston assemblies respectively associated with the cylinders of the engine assembly, said method comprising the steps of;
   (A) rotating the crankshaft of the engine assembly;
   (B) generating a plurality of code signals for each rotation of the crankshaft in timed relation to the crankshaft rotation;
   (C) sensing the level of acoustical vibration in the vicinity of the engine assembly during rotation of the crankshaft;
   (D) generating a fault signal in response to a sensed acoustical vibration in excess of a predetermined magnitude to indicate that a part is missing in the engine assembly; and
   (E) comparing said code signals and said fault signal on a time line basis to determine the particular piston assembly from which the part is missing.

2. A method according to claim 1 wherein:
said code signals are generated by an angle encoder operative to generate
   (1) a plurality of equally spaced pulse signals for each revolution of the crankshaft, and
   (2) a marker signal each time the crankshaft passes through a given angular position.

3. A method according to claim 2 wherein:
the crankshaft is rotated by a motor; and
the motor also drives the angle encoder.

4. A method according to claim 3 wherein:
the crankshaft of the engine assembly includes a key means;
the motor engages the end of the crankshaft and locates on the crankshaft at a fixed angular position related to the angular position of the crankshaft key means; and
the marker signal is generated at a fixed angular position related to the angular position of the crankshaft key means.

5. An appartus for detecting missing or misplaced parts in a multicylinder engine assembly of the type including a crankshaft and a plurality of piston assemblies associated with the respective cylinders, said apparatus comprising:
   (A) an acoustical pick-up device adapted to be positioned adjacent the engine assembly and operative to generate a fault signal in response to a sensed acoustical vibration of a predetermined intensity;
   (B) a drive motor adapted to be moved into engagement with the crankshaft of the engine assembly to rotate the crankshaft and move the piston assemblies of the various cylinders through their reciprocal cycles;
   (C) an angle encoder operative to generate a plurality of code signals for each revolution of the crankshaft;
   (D) a plurality of indicator means respectively corresponding to the cylinders of the engine assembly; and
   (E) means receiving said code signals and said fault signal and operative to selectively activate or fail to activate each of said indicator means depending on the presence or absence of a fault signal at the point of rotation of the crankshaft corresponding to a transitional position in the reciprocal cycle of the piston assembly operating in the corresponding cylinder of the engine assembly.

6. An apparatus according to claim 5 wherein:
(F) said angle encoder is driven by said motor.

7. An apparatus according to claim 6 wherein:
(G) said angle encoder is operative to generate
   (1) a plurality of equally spaced pulse signals for each revolution of the crankshaft, and
   (2) a marker signal each time the crankshaft passes through a given angular position.

8. An apparatus according to claim 7 wherein:
(H) the crankshaft of the engine assembly includes key means;
(I) said drive motor engages the end of the crankshaft and locates on the crankshaft at a fixed angular position related to the angular position of the crankshaft key means; and
(J) said marker signal is generated at a fixed angular position related to the angular position of the crankshaft key means.

9. An apparatus for detecting missing parts in multicylinder engine assemblies moving along an assembly line and each including a block and a crankshaft, said apparatus comprising:
   (A) an acoustical pick-up device positioned at a work station along the assembly line and operative to generate a noise signal in response to sensed acoustical vibrations;
   (B) means mounting said pick-up device for movement between a rest position and a working position adjacent the block of an engine assembly positioned at the work station;
   (C) a motor positioned at said work station and including a drive shaft and a driver secured to the free end of said drive shaft;
   (D) means mounting said motor for movement between a rest position and a working position in which said driver drivingly engages the near end of the crankshaft of an engine assembly positioned at the work station;

(E) an angle encoder operative to generate a plurality of code signals for each revolution of the crankshaft of the engine assembly;

(F) a plurality of indicator means respectively corresponding to the cylinders of the engine assembly; and (G) a comparator receiving said code signals and said noise signal and operative to selectively activate or fail to activate each of said indicator means depending on whether said noise signal is in excess of a predetermined magnitude at the point of rotation of the crankshaft corresponding to a transitional position of the piston assembly operating in the corresponding cylinder of the engine assembly.

10. An apparatus according to claim 9 wherein:

(H) said encoder is operative to generate
 (1) a plurality of equally spaced pulse signals for each revolution of the crankshaft, and
 (2) a marker signal each time the crankshaft passes through a given angular position.

11. An apparatus according to claim 10 wherein:

(I) the crankshaft of the engine assembly includes a key means;

(J) said driver engages the end of the crankshaft and locates on the crankshaft at a fixed angular position related to the angular position of the crankshaft key means; and (K) said marker signal is generated at a fixed angular position related to the angular position of the crankshaft key means.

12. An apparatus according to claim 9 wherein:

(L) said apparatus further includes a carrier mounted for movement relative to the assembly line; and (M) said motor, said encoder, and said acoustical pick-up device are mounted on said carrier.

13. An apparatus according to claim 12 wherein:

(N) said encoder is driven by said motor.

14. An apparatus for detecting missing parts in multicylinder engine assemblies moving along an assembly line and each including a block and a crankshaft, said apparatus comprising:

(A) an acoustical pick-up device, including a pair of microphones, positioned at a work station along the assembly line and operative to generate a noise signal in response to sensed acoustical vibrations;

(B) a carrier mounting said pick-up device for movement between a rest position and a working position adjacent the block of an engine assembly positioned at the work station;

(C) a motor, including a drive shaft and a driver secured to the free end of said drive shaft, mounted on said carrier for movement between a rest position and a working position in which said driver drivingly engages the near end of the crankshaft of an engine assembly positioned at the work station;

(D) an angle encoder mounted on said carrier, driven by said motor, and operative to generate a plurality of code signals for each revolution of the crankshaft of the engine assembly;

(E) a plurality of indicator means respectively corresponding to the cylinders of the engine assembly; and (F) a comparator receiving said code signals and said noise signals and operative to selectively activate or fail to activate each of said indicator means depending on the presence or absence of a noise signal in excess of a predetermined magnitude at the point of rotation of the crankshaft corresponding to a transitional position of the piston assembly operating in the corresponding cylinder of the engine assembly;

(G) said apparatus being for use with engine assemblies of the V-8 type and said carrier including a portion positioning said microphones in spaced relation over the engine assembly with said driver engaging the crankshaft of the engine assembly.

15. An apparatus according to claim 14 wherein:

(Q) said carrier portion positions said microphones one adjacent the engaged end of the crankshaft and the other adjacent the other end of the crankshaft.

* * * * *